United States Patent [19]

Jana et al.

[11] Patent Number: 5,318,929
[45] Date of Patent: Jun. 7, 1994

[54] APATITE GLASS CERAMIC

[75] Inventors: Carsten Jana; Wolfram Höland, both of Jena-Winzerla; Werner Vogel, Jena, all of Fed. Rep. of Germany

[73] Assignee: Thera Patent GmbH & Co. KG Gesellschaft für Industrielle Schutzrechte, Seefeld, Fed. Rep. of Germany

[21] Appl. No.: 768,920

[22] PCT Filed: Feb. 11, 1991

[86] PCT No.: PCT/EP91/00265
§ 371 Date: Oct. 10, 1991
§ 102(e) Date: Oct. 10, 1991

[87] PCT Pub. No.: WO91/12212
PCT Pub. Date: Aug. 22, 1991

[30] Foreign Application Priority Data

Feb. 12, 1990 [DE] Fed. Rep. of Germany ....... 3377650

[51] Int. Cl.⁵ .................. C03C 10/02; C03C 10/16
[52] U.S. Cl. ........................... 501/10; 501/3; 501/73; 106/35
[58] Field of Search ............. 106/35; 501/3, 10, 73; 433/228.1

[56] References Cited

U.S. PATENT DOCUMENTS

| | | | |
|---|---|---|---|
| 3,814,717 | 6/1974 | Wilson et al. | 106/35 X |
| 4,089,830 | 5/1978 | Tezuka et al. | |
| 4,360,605 | 11/1982 | Schmitt et al. | |
| 4,376,835 | 3/1983 | Schmitt et al. | |
| 4,527,979 | 7/1985 | McLean et al. | 106/35 X |
| 4,643,982 | 2/1987 | Kasuga et al. | |
| 4,877,402 | 10/1989 | Hirabayashi et al. | 106/35 X |
| 4,900,697 | 2/1990 | Akahane et al. | |
| 4,960,733 | 10/1990 | Kasuga et al. | 501/10 |

FOREIGN PATENT DOCUMENTS

| | | |
|---|---|---|
| 0023013 | 1/1981 | European Pat. Off. |
| 0024056 | 2/1981 | European Pat. Off. |
| 3804469 | 8/1988 | Fed. Rep. of Germany |
| 52-101893 | 8/1977 | Japan |

*Primary Examiner*—Karl Group
*Attorney, Agent, or Firm*—Birch, Stewart, Kolasch & Birch

[57] ABSTRACT

The invention relates to an apatite glass ceramic which can be used as a biomaterial in medicine and as an inorganic component of a glass ionomer cement. The apatite glass ceramic comprises in wt-%) 15-40% $SiO_2$, 15-35% $Al_2O_3$, 12-30% CaO, 6-25% $P_2O_5$, 2.5-15% $F^-$, 0-18% $R_2O$, wherein $R_2O$ is an alkali oxide. The apatite glass ceramic comprises a crystal phase which contains apatite.

1 Claim, No Drawings

APATITE GLASS CERAMIC

FIELD OF THE INVENTION

The invention relates to an apatite glass ceramic, which due to its properties can be used as a biomaterial in medicine particularly in stomatology or as in inorganic component for glass ionomer cements.

BACKGROUND OF THE INVENTION

Apatite-containing glass ceramics and apatite sintered ceramics are known and are, e.g., described in DD 219 017 and in DD 245 864. Such biomaterials form direct bonds to living bones.

However, as an inorganic component in ionomer cements, special requirements are made of a glass ceramic. Apatite-containing glass ceramics for glass ionomer cements have not yet been developed. Glass ionomer cements are formed by mixing fluoroalumosilicate glass powder with polymeric carboxylic acids. Glass ionomer cements are used in stomatology for suitable indications such as underfilling, stump reconstruction and securing.

A combination consisting solely of fluoroalumosilicate glass powders and polyacrylic acid gives glass ionomer cements with poor processing properties. The glass ionomer cement takes too long to set completely, so that its surface becomes brittle as a result of contact with saliva in the mouth of the patient. To overcome these disadvantages the Japanese Patent 52 (1977) 101 893, for example, discloses an aqueous polyacrylic acid or acrylic polymer solution, which contains one or more polybasic carboxylic acids. By using this liquid, shorter setting times and greater mechanical strengths are achieved. U.S. Pat. No. 4,360,605 discloses a hardening liquid which contains, in addition to an acrylic acid copolymer, tartaric acid. It was ascertained that with this the ratio of processing time to setting time was further improved. With glass ionomer cements the processing time should be long and the setting time as short as possible. In this respect, these glass ionomer cements still do not fulfil the requirements of the user.

With glass ionomer cements the setting process is characterized by the formation of calcium and aluminium polycarboxylates. In the first reaction step a still relatively water-sensitive calcium polycarboxylate forms, and only the formation of aluminium polycarboxylate, which takes place later due to its higher degree of order and the lower migration speed of the more highly-charged aluminium ions, leads to a stable cement system. Fluoroalumosilicate glass powders of the $SiO_2-Al_2O_3-CaO-P_2O_5-Na_2O-F^-$ system according to U.S. Pat. No. 4,376,835 have the disadvantage that bending strength and adhesion on the hard dental substance are inadequate. According to Wilson and Mclean [Glass Ionomer Cement, Quintessenz-Verlag Berlin (West) 1988, 28], the function of the calcium ions in the setting process can be taken over by strontium ions. Strontium-containing fluoroalumosilicate glass powders according to DE-A 3 804 469 admittedly show improved properties with regard to solubility and X-ray visibility, but display insufficient bending strengths and adhesion on the hard dental substance.

Wilson and colleagues (Ind. Eng. Chem. Prod. Res. Dev. 19, 1980, 263-270) investigated glasses in which $CaF_2$ crystals formed in a secondary process. It was ascertained that these glasses have a lower mechanical strength than the corresponding clear glasses.

SUMMARY OF THE INVENTION

The aim of the invention is to develop an apatite-containing glass ceramic, which can be used in particular in forming glass ionomer cement and biomaterials which improves manipulability and adhesion vis-à-vis known technical solutions of glass ionomer cements.

The aim is achieved according to the invention in that the apatite glass ceramic contains the composition

| | |
|---|---|
| $SiO_2$ | 15-40 wt % |
| $Al_2O_3$ | 15-35 wt % |
| CaO | 12-30 wt % |
| $P_2O_5$ | 6-25 wt % |
| $F^-$ | 2.5-15 wt % |
| $R_2O$ | 0-18 wt %, | wherein the wt-%'s are calculated on the basis of the oxides, $R_2O$ being an alkali oxide—preferably $Na_2O$—and, in addition to the glass phase, the glass ceramic containing a crystal phase apatite. The apatite is preferably contained as the main crystal phase. In addition, e.g., sillimanite, cristobalite and fluorite can also be contained therein. Sillimanite and cristobalite can also form the main crystal phase. Up to 25 wt-% of additional components such as, e.g., SrO, FeO, $Fe_2O_3$, $La_2O_3$, $TiO_2$ can likewise be contained therein, either individually or as a mixture. The additional components are added in order to advantageously influence the glass ceramic with regard to properties such as coloration, X-ray visibility, opacity, translucence. The composition is preferably as follows:

| | |
|---|---|
| $SiO_2$ | 15-40 wt % |
| $Al_2O_3$ | 15-35 wt % |
| CaO | 12-30 wt % |
| $P_2O_5$ | 8-25 wt % |
| $F^-$ | 3-12 wt % |
| $R_2O$ | 3.5-16 wt %. |

The following composition is especially preferred:

| | |
|---|---|
| $SiO_2$ | 15-40 wt % |
| $Al_2O_3$ | 15-35 wt % |
| CaO | 12-30 wt % |
| $P_2O_5$ | 8-25 wt % |
| $F^-$ | 4-11 wt % |
| $R_2O$ | 6-10 wt %. |

If $R_2O$ signifies $K_2O$, the apatite glass ceramic preferably contains a maximum of 8 wt-%, particularly a maximum of 5 wt-% $K_2O$.

The crystal phase apatite increases the mechanical strength and stimulates the bone growth. Preferably contained in the apatite glass ceramic according to the invention are fluorapatite and also hydroxyl apatite or mixed fluor-hydroxyl apatite. In these apatite phases, sodium ions and/or potassium ions and/or aluminium ions and/or strontium ions can also be incorporated.

DETAIL DESCRIPTION OF THE INVENTION

The glass ceramic material according to the invention is prepared from a starting glass that is melted at 1450° C. to 1600° C. It was surprisingly ascertained that the glasses possess droplet-shaped demixing areas, often with multi-demixing, and precipitate apatite crystals upon subsequent temperature treatment. This is all the more surprising because in other composition ranges a regulated precipitation of apatite crystals via an amorphous/amorphous phase separation is not realizable.

The starting glass is cooled to below the transformation temperature or subjected to a regulated crystallization direct from the melt. The regulated crystallization takes place by single-step thermal treatment of the glasses in the temperature range 700° C. to 1150° C. The crystallization process of the starting glass to form the glass ceramic according to the invention is regulated by specifically influencing the phase separation of the glasses.

The apatite crystals in the glass are precipitated from $Ca^{2+}$—$P_2O_5$—$F^-$-rich, droplet-shaped primary demixing areas. Through selection of the chemical composition, of the melting conditions and of the thermal treatment, volume proportion, number and size of these demixing areas can be set., thus volume proportion and crystal size of the apatite phase are regulable. According to the invention, the apatite crystals of the apatite glass ceramic preferably have a crystal size of 0.2 to 3 µm.

For the use of the apatite glass ceramic according to the invention as an inorganic component in a glass ionomer cement, a powder of the glass ceramic is used, the powder grains preferably having an average grain size (weight average) of at least 1 µm and preferably at least 3 µm. The average grain size (weight average) is 1–20 µm, preferably 3–15 µm and especially preferably 3–10 µm. The particles have a maximum grain size of 150 µm, preferably 100 µm, more preferably 60 µm.

strontium salts are practically no longer located on the surface of the powder particles.

As polyacids, the polyacids known in connection with glass ionomer cement can be used, e.g., polymaleic acid, polyacrylic acid, polyitaconic acid and mixtures thereof, or copolymers, particularly the maleic acid-acrylic acid copolymers and/or acrylic acid-itaconic acid copolymers known from EP-B-0 024 056. The average molecular weight of the polycarboxylic acids to be used according to the invention is more than 500. An average molecular weight of 1,000 to 20,000 is advantageous, especially preferred are 3,000 to 10,000. The polycarboxylic acid is preferably used in concentrations of 5 to 50 wt-%, relative to the weight of the apatite glass ceramic. Also suitable as the polyacid are polyphosphonic acids, e.g. polyvinyl phosphonic acid. These polyphosphonic acids can partly or wholly replace the aforementioned polycarboxylic acids.

It was surprisingly ascertained that glass ionomer cements prepared from apatite glass ceramic powder have better processing properties, speedy hardening and an increased mechanical strength. The presence of the apatite crystal phase effects a better adhesion of the glass ionomer cement on the hard dental substance.

EXEMPLARY EMBODIMENTS

Table 1 gives an overview of the compositions in wt-% of apatite glass ceramic, or their starting glasses, according to the invention. Table 2 contains selected examples which show the relationship between chemical composition, thermal treatment of the starting glasses and crystal phase, crystal size.

TABLE 1

Compositions of the apatite glass ceramic or of its starting glasses

| Ex. No. | $SiO_2$ | $Al_2O_3$ | CaO | $P_2O_5$ | $Na_2O$ | $F^-$ | SrO | $Fe_2O_3$ | $K_2O$ | $La_2O_3$ |
|---|---|---|---|---|---|---|---|---|---|---|
| 1 | 15.2 | 34.6 | 24.3 | 15.7 | 6.1 | 4.1 | — | — | — | — |
| 2 | 15.3 | 15.2 | 24.5 | 24.1 | 15.7 | 5.2 | — | — | — | — |
| 3 | 39.8 | 15.3 | 12.7 | 8.2 | 14.0 | 10.0 | — | — | — | — |
| 4 | 22.0 | 26.4 | 20.5 | 15.6 | 6.2 | 9.3 | — | — | — | — |
| 5 | 26.3 | 20.2 | 28.1 | 9.4 | 6.1 | 9.9 | — | — | — | — |
| 6 | 23.9 | 24.8 | 14.3 | 17.7 | 7.3 | 7.1 | 4.9 | — | — | — |
| 7 | 21.0 | 17.9 | 23.9 | 12.3 | 11.9 | 9.0 | 3.6 | 0.4 | — | — |
| 8 | 19.8 | 23.6 | 25.7 | 15.8 | 7.7 | 7.4 | — | — | — | — |
| 9 | 22.1 | 22.8 | 19.1 | 16.0 | 9.6 | 6.5 | — | — | 3.9 | — |
| 10 | 31.4 | 28.5 | 13.0 | 8.5 | 9.6 | 9.0 | — | — | — | — |
| 11 | 22.0 | 26.8 | 20.2 | 15.8 | 8.2 | 7.0 | — | — | — | — |
| 12 | 27.3 | 24.7 | 18.7 | 12.9 | 8.0 | 8.4 | — | — | — | — |
| 13 | 23.4 | 15.9 | 19.3 | 14.6 | 9.4 | 9.4 | — | — | — | 8.0 |
| 14 | 24.9 | 25.8 | 20.0 | 18.4 | 3.5 | 7.4 | — | — | — | — |
| 15 | 25.8 | 26.7 | 20.7 | 19.1 | — | 7.7 | — | — | — | — |
| 16 | 24.5 | 16.8 | 16.4 | 18.3 | 16.2 | 7.8 | — | — | — | — |
| 17 | 23.4 | 23.9 | 19.3 | 14.6 | 9.4 | 9.4 | — | — | — | — |

The glass ionomer cement is prepared by hardening this glass ceramic powder and a polyacid in the presence of water and optionally other usual additives, such as e.g., tartaric acid. The resultant powders are then optionally subjected to a surface treatment as per European Patent 0 023 013. To this end the glass powders are treated on the surface with acid, preferably at room temperature. Acid-group-containing substances are used, e.g., hydrochloric acid, sulphuric acid, nitric acid, acetic acid, propionic acid or perchloric acid, which form soluble calcium salts or strontium salts. The acids are used in a concentration of 0.01 to 10 wt-%, preferably of 0.05 to 3 wt-%. After the corresponding reaction time, the powders are separated from the solution and thoroughly washed out, so that soluble calcium or

TABLE 2

Thermal treatment of the starting glasses and resultant crystal phases and crystallite sizes

| Ex. No. | Thermal treatment | Crystal phase | Crystal size |
|---|---|---|---|
| 8 | 950° C./1 h | apatite | 0.2–0.6 µm |
| 8 | 1050° C./1 h | apatite | 0.5–1 µm |
| 8 | 1150° C./1 h | apatite | 1.5–4 µm |
| 9 | 900° C./2 h | apatite | 0.3–0.7 µm |
| 10 | 950° C./2 h | apatite | 0.7–2 µm |
| 11 | 800° C./1 h | apatite | 0.2–0.3 µm |
| 14 | 920° C./2 h | apatite (main phase) cristobalite, sillimanite (secondary phases) | <2 µm |
| 15 | 920° C./2 h | cristobalite, stillimanite (main phases) apatite | <2 µm |

TABLE 2-continued

Thermal treatment of the starting glasses and resultant crystal phases and crystallite sizes

| Ex. No. | Thermal treatment | Crystal phase | Crystal size |
|---|---|---|---|
|  |  | (secondary phase) | 2 μm |
| 16 | 910° C./2 h | apatite | 0.25–0.7 μm |
| 17 | 910° C./2 h | apatite | 0.25–0.35 μm |

EXAMPLE 18

The glass ceramic of example 16, thermally treated as per Table 2, was ground to a fine powder with an average grain size of 6.2 μm (weight average); the maximum grain size was 40 μm.

1 g of this powder was mixed with 0.33 g of an aqueous polycarboxylic acid solution of the following composition:

50 parts by weight water
40 parts by weight of a copolymer comprising acrylic acid and maleic acid (1:1, average molecular weight 13,000)
10 parts by weight tartaric acid At 23° C. room temperature the cement mixture obtained was plastically deformable for 3 minutes 15 seconds (processing time) and had already hardened after 3 minutes 20 seconds (hardening time), calculated in each case from the commencement of mixing.

After 24 hours' hardening at 36° C., the bending strength was 39.7 MPa.

EXAMPLE 19

The glass ceramic of example 17, thermally treated as per Table 2, was ground to a fine powder with an average grain size of 7.8 μm (weight average); the maximum grain size was 45 μm.

1 g of this powder was mixed with 0.33 g of the aqueous polycarboxylic acid from example 18.

At 23° C. room temperature, the cement mixture obtained had a processing time of 2 minutes 40 seconds and a hardening time of only 3 minutes 55 seconds, calculated in each case from the commencement of mixing.

After 24 hours' hardening at 36° C., the bending strength was 34.9 MPa.

We claim:

1. In a glass ionomer cement prepared by hardening a glass ceramic powder and a polyacid in the presence of water, the improvement comprising an apatite glass ceramic powder comprising:

| | |
|---|---|
| $SiO_2$ | 15–40 wt %, |
| $Al_2O_3$ | 15–35 wt %, |
| CaO | 12–30 wt %, |
| $P_2O_5$ | 6–25 wt %, |
| $F^-$ | 2.5–15 wt %, |
| $R_2O$ | 0–18 wt % and | up to 25 wt-% of additional components selected from the group consisting of SrO, $La_2O_3$, FeO, $Fe_2O_3$, $TiO_2$ and mixtures thereof; wherein the wt-%'s are calculated on the basis of the oxides; $R_2O$ is an alkali oxide; and wherein the composition contains a crystal phase comprising apatite.

* * * * *